United States Patent [19]

Finkelstein et al.

[11] Patent Number: 5,328,845
[45] Date of Patent: Jul. 12, 1994

[54] FUNGAL NEGATIVE MICROORGANISM CAPABLE OF PRODUCING HIGH LEVELS OF BETA-CAROTENE

[75] Inventors: Mark Finkelstein, Ft. Collins, Colo.; Chien-Chang Huang, Taipei, Taiwan; Graham S. Byng, Woodinville, Wash.; Bi-Ru Tsau, Taipei Hsien, Taiwan; Jeanette Leach, Boulder, Colo.

[73] Assignee: Universal Foods Corporation, Milwaukee, Wis.

[21] Appl. No.: 858,147

[22] Filed: Mar. 27, 1992

[51] Int. Cl.$^5$ ............................................. C12N 1/14
[52] U.S. Cl. .................................. 435/254.1; 435/67; 435/171; 435/911
[58] Field of Search ..................... 435/254, 67

[56] References Cited

U.S. PATENT DOCUMENTS

| | | | |
|---|---|---|---|
| 2,865,814 | 12/1958 | Hesseltine et al. | 435/42 |
| 2,890,989 | 6/1959 | Anderson | 435/67 |
| 2,910,410 | 10/1959 | Corman | 435/67 |
| 2,959,521 | 11/1960 | Zajic | 435/67 |
| 2,959,522 | 11/1960 | Zajic | 435/67 |
| 3,001,912 | 9/1961 | Miescher | 435/67 |
| 3,095,357 | 6/1963 | Fulde | 435/67 |
| 3,226,302 | 12/1965 | Ciegler | 435/67 |
| 3,235,467 | 2/1966 | Ninet et al. | 435/67 |
| 3,242,054 | 3/1966 | Ninet et al. | 435/67 |
| 3,291,701 | 12/1966 | Fulde | 435/67 |
| 3,378,460 | 4/1968 | Ninet et al. | 435/67 |
| 3,421,980 | 1/1969 | Ninet et al. | 435/67 |
| 3,492,202 | 1/1970 | Bohinski | 435/67 |
| 3,522,146 | 7/1970 | Jager | 435/167 |
| 4,318,987 | 3/1982 | Murillo et al. | 435/172 |

OTHER PUBLICATIONS

Candau et al., "In Vivo channeling of Substrates in an Enzyme Aggregate for β-carotene Biosynthesis," PNAS, vol. 88, pp. 4936–4940, 1991.
Jacobson, G., "Mutations", Biotechnology, vol. 1, Rehm et al. eds.; Published by Verlag Chemie, 1981.
Creuger, W. et al., "Strain Development", In Biotechnology: A Textbook of Industrial Microbiology, Published: Sinaw Associates, pp. 9–17, 1984.
Lewis, M. J. et al., "Selection of Astaxanthin-Overproducing Mutants of *Phaffia rhodozyma* with β-Ionone", Appl. Environment Microbiol, vol. 56, No. 9, pp. 2944–2945, 1990.
Nelis et al., "Microbial Sources of Carotenoid Pigments Used in Foods and Feeds", pp. 181–191, 1991, Journal of Applied Bacteriology, vol. 70.
Murillo et al., "Carotene-Superproducing Strains of *Phycomyces*", pp. 639–642, 1978, Appl. Environ. Microbiol., vol. 36.
Salgado et al., "Carotene-Superproducing Mutants of *Phycomyces blakesleeanus*", pp. 332–336, 1989, Experimental Mycology, vol. 13.
Lampila et al., "A Review of Factors Affecting Biosynthesis of Carotenoids by the Order Mucorales", pp. 65–80, 1985, Mycopathologia, vol. 90.
Cerda-Olmedo, "Production of Carotenoids with Fungi", pp. 27–42, 1989, Biotechnology of Vitamins, Pigments, and Growth Factors, (E. Vandamme, ed).

*Primary Examiner*—Marian Knode
*Attorney, Agent, or Firm*—Whyte Hirschboeck Dudek

[57] ABSTRACT

The present invention is directed toward a method for producing beta-carotene using negative (minus mating type) Mucorales fungal microorganisms. The method includes mutating and selecting negative Mucorales fungal microorganisms, culturing the selected negative microorganisms in an effective medium to produce beta-carotene, and recovering beta-carotene therefrom. The present invention provides negative microorganisms that overproduce beta-carotene, beta-carotene formulations produced by the disclosed method, and the use of such formulations to enhance pigmentation, to reduce damage caused by reactive oxygen species or phototoxic molecules, to prevent or treat cancer or cardiovascular disease, to provide a Vitamin A supplement, to enhance lactation, and to increase fertility.

22 Claims, No Drawings

FUNGAL NEGATIVE MICROORGANISM CAPABLE OF PRODUCING HIGH LEVELS OF BETA-CAROTENE

FIELD OF THE INVENTION

The present invention relates generally to a method for producing beta-carotene and to certain fungal microorganisms capable of producing improved yields of beta-carotene. More particularly, the invention relates to the production of beta-carotene by fermenting novel minus mating type (negative) Blakeslea trispora microorganisms.

BACKGROUND OF THE INVENTION

The carotenoid beta-carotene is a pigment useful in enhancing the pigmentation of animal foodstuffs, food products and cosmetics. Typically, beta-carotene provides yellow to yellow-orange pigmentation. Beta-carotene also serves as a precursor of Vitamin A (retinol) in both animals and man. In addition, beta-carotene, like some other carotenoids, is an effective antioxidant. Epidemiological studies suggest the use of beta-carotene to prevent or treat certain types of cancer and to reduce cellular or tissue damage caused by reactive oxygen species and phototoxic molecules, as occurs, for example, in cardiovascular disease. Beta-carotene may also be used to stabilize compounds subject to oxidation, particularly when exposed to light.

Due to Food and Drug Administration regulations covering chemically-synthesized products, it is preferable to use biological sources to produce beta-carotene. The carotenoid is known to be synthesized by most green plants as well as by certain algae (e.g., Dunaliella), fungi (e.g., Ascomycetes and Deuteromycetes), cyanobacteria and photosynthetic bacteria. Naturally-occurring Zygomycetes of the order Mucorales, family Choanephoraceae, which includes the genera Blakeslea, Choanephora, Mucor, Parasitella, Phycomyces, and Pilaria are particularly well known producers of beta-carotene. Accumulation of beta-carotene in these fungi is strongly linked to sexual interaction between plus mating type (positive) and minus mating type (negative) microorganisms of such fungi. In one example using wild-type Blakeslea trispora, a negative microorganism alone produced 108 milligrams of beta-carotene per liter of medium while a mated culture, formed from the same negative microorganism and a positive microorganism, produced 350 milligrams of beta-carotene per liter of medium (U.S. Pat. No. 3,522,146 by Jager, issued Jul. 28, 1970). In a second example using Phycomyces, a negative microorganism alone produced 5.6 milligrams of beta-carotene per gram dry cell weight while a mated culture, formed between the negative microorganism and a positive microorganism, produced 25 milligrams of beta-carotene per gram dry cell weight (U.S. Pat. No. 4,318,987 by Murillo Araujo et al., issued Mar. 9, 1982).

Investigators have shown that beta-factor, a hormone-like substance that is produced upon mating, stimulates beta-carotene production in Blakeslea. The major component of beta-factor is trisporic acid. Other chemicals that stimulate beta-carotene production include beta-ionone, retinol, kerosene, aromatics (such as dimethyl phthalate and veratrol), and nitrogenous heterocyclic compounds (such as isoniazid and iproniazid). However, past efforts to produce beta-carotene have focussed primarily on improving fermentation conditions rather than on the use of genetic selection techniques to improve beta-carotene production.

SUMMARY OF THE INVENTION

The present invention is directed toward a method for producing beta-carotene which includes mutating negative Mucorales fungal microorganisms, selecting from the mutated microorganisms a negative microorganism capable of producing at least about 0.15 grams of beta-carotene per liter of medium in about 7 days, culturing the selected microorganism in an effective production fermentation medium to produce beta-carotene, and recovering beta-carotene therefrom.

The present invention provides negative microorganisms that overproduce beta-carotene. Preferred methods for selecting such negative microorganisms include color of the microorganism and ability of the microorganism to grow in the presence of an effective selective agent. Microorganisms of the present invention preferably are able to produce at least about 0.5 grams of beta-carotene per liter in about 7 days, more preferably at least about 1.5 grams of beta-carotene per liter in about 7 days, and even more preferably at least about 3 grams of beta-carotene per liter in about 7 days. Preferred microorganisms of the present invention are of the genus Blakeslea, including B. trispora ATCC No. 74146 (PF17-12), B. trispora ATCC No. 74147 (PF17-13), and mutants of either of those microorganisms.

The present invention also provides beta-carotene-containing biomasses and other beta-carotene-containing formulations produced by the disclosed method. Beta-carotene produced according to the present invention can be used to enhance the pigmentation of animal foodstuffs, other food products, and cosmetics; to reduce damage caused by reactive oxygen species or phototoxic molecules; to prevent or treat cancer or cardiovascular disease; to provide a Vitamin A supplement; to enhance lactation; and to increase fertility.

DETAILED DESCRIPTION OF THE INVENTION

Mucorales fungal microorganisms exhibit both asexual and sexual modes of reproduction. Mucorales fungi generally exist as non-mated microorganisms of opposite mating types. As used herein, a "non-mated microorganism" is a microorganism that is either of a negative (minus) or a positive (plus) mating type depending on its sexual characteristics. Both negative and positive microorganisms can be either spores or mycelia depending on the stage of the fungal life cycle. For example, during the asexual mode of replication, a non-mated microorganism spore germinates into a mycelium. When the mycelium has grown to an appropriate size, it produces aerial hyphae containing sporangia filled with spores. During the sexual mode of reproduction, a negative microorganism interacts with a positive microorganism to form a mated culture.

Without being bound by theory, it is believed that this sexual interaction triggers signals by negative and/or positive microorganisms that stimulate beta-carotene production by the culture. While negative microorganisms typically produce significantly more beta-carotene than do positive microorganisms, the highest levels of beta-carotene production generally occur when the negative and positive microorganisms are physically together (i.e., mated). For example, it is known that wild-type mated cultures of negative and positive Mucorales fungal microorganisms are capable of producing at least about 5- to 20-times as much beta-carotene as are wild-type non-mated microorganisms. However, mated cultures are not stable, and, thus, each fermentation to produce beta-carotene requires the culturing of positive and negative microorganisms in separate fermentations until each grows to an effective cell density, followed by the mixing together (or mating) of the negative and positive microorganisms to form a mated culture that produces beta-carotene.

Since non-mated Mucorales fungal microorganisms are more stable than mated cultures and since non-mated negative microorganisms typically produce significantly more beta-carotene than do non-mated positive microorganisms, it is preferable to target negative microorganisms for genetic strain improvement to produce a microorganism that overproduces beta-carotene. An advantage of using an non-mated negative microorganism to produce beta-carotene is that such a microorganism might be used in continuous or semi-continuous fermentation procedures. Use of an non-mated negative microorganism also obviates the need to regulate the mating parameters (e.g., matching cell densities, identifying appropriate mating ratios) of negative and positive microorganisms to form mated cultures that are capable of overproducing beta-carotene.

In one aspect of the present invention, mutation and selection strategies herein described are used to genetically improve negative Mucorales fungal microorganisms, resulting in the production of negative Mucorales fungal microorganisms that are capable of overproducing beta-carotene when cultured in an effective production fermentation medium. Such a production fermentation medium includes an effective amount of beta-factor to stimulate beta-carotene production. As used herein, a "negative microorganism capable of overproducing beta-carotene" is a negative Mucorales fungal microorganism that is capable of producing at least about 0.15 grams of beta-carotene per liter in about 7 days when cultured in an effective production fermentation medium, even though the negative microorganism has not been mated to a positive microorganism. Preferably, a negative microorganism capable of overproducing beta-carotene is capable of producing at least about 0.5 grams of beta-carotene per liter of effective production medium in about 7 days and at least about 12.5 mg of beta-carotene per gram dry cell weight when cultured in an effective production fermentation medium.

Surprisingly, negative microorganisms of the present invention when cultured in an effective production fermentation medium are capable of producing at least about 50% as much beta-carotene as when they are mixed together with positive Mucorales fungal microorganisms to form a mated culture that is cultured to produce beta-carotene.

As used herein, a "parental Mucorales fungal microorganism" refers to any negative Mucorales fungal microorganism that is to be mutated with the object of obtaining a microorganism that is capable of producing more beta-carotene than the parental microorganism. Negative parental microorganisms include, but are not limited to, naturally-occurring (wild-type), variant, previously mutated, and previously selected microorganisms. In the present invention, preferred parental microorganisms are negative Mucorales fungi of the family Choanephoraceae, particularly microorganisms of the genus Blakeslea, and more particularly microorganisms of the species *Blakeslea trispora*.

As used herein, a "mutated microorganism" is a negative Mucorales fungal microorganism in which a mutation either occurs naturally or results from intentional exposure of the microorganism to a mutagen. In a preferred embodiment of the present invention, a negative parental microorganism is subjected to at least one round of chemical or physical mutagenesis in order to increase the mutation rate, thereby increasing the probability of obtaining a desired microorganism.

In accordance with the present invention, a negative parental Mucorales fungal microorganism is mutated using any suitable mutagen in order to obtain a mutated microorganism. Suitable mutagens include, but are not limited to, N-methyl-N'-nitro-N-nitrosoguanidine (NTG), ethylmethane sulfonate (EMS), nitrous acid, nucleotide analogs, acridines, ultraviolet light (UV), x-rays, gamma rays, and mixtures thereof.

In a preferred embodiment of the present invention, an effective amount of the mutagen NTG is added to a spore suspension of a negative parental microorganism of *Blakeslea trispora*. The spores are incubated in a buffer medium, such as Tris(hydroxymethyl)-aminomethane (Tris) at a pH of about 8.0, containing from about 10 micrograms ($\mu g$) to about 500 $\mu g$ NTG per milliliter (ml) medium for a period of time from about 10 minutes to about 30 minutes at about room temperature. Preferably, *B. trispora* spores are exposed to about 50 $\mu g$ NTG per ml of medium for about 20 minutes at about room temperature. After exposure, mutated spores are plated onto a solidified growth medium at about 26° C. to about 28° C., preferably at about 27° C., for about 5 to about 10 days to obtain separate colonies. As used herein, a solidified growth medium refers to a growth medium to which a solidifying agent such as gelatin, agarose, or agar has been added. A preferred solidified growth medium of the present invention is CM17-1, which is an aqueous medium containing glucose, magnesium sulfate, potassium phosphate, L-asparagine, thiamine, yeast extract, and sodium-deoxycholate, to which agar has been added.

In accordance with the present invention, a desired negative microorganism is selected from among all mutated microorganisms. As used herein, a "selected microorganism" refers to a mutated negative microorganism which is capable of producing more beta-carotene than a parental microorganism. In one embodiment of the present invention, a negative mutated microorganism displaying a pigmentation (i.e., color) indicative of an ability to produce beta-carotene is selected. As used herein, "a pigmentation indicative of the ability to produce beta-carotene" includes the colors pale yellow, yellow, yellow-orange, orange, red-orange and red, depending on the selection regimen. For example, red microorganisms may be selected when a selective agent that inhibits the synthesis of beta-carotene from the red pigment lycopene is used. A preferred pigmentation color range for selection of desired negative mutated microorganisms is from about deep yellow to about yellow-orange.

Alternatively, or in addition, a desired mutated microorganism may be selected by its ability to grow in the presence of an effective amount of a selective agent (i.e., by its ability to be resistant to said selective agent). As used herein, an "effective amount of a selective agent" is an amount that typically inhibits the growth of parental microorganisms to a greater extent than the growth of a desired microorganism. Effective selective agents include, but are not limited to, antihypercholesterolemic agents, antihyperlipoproteinemic agents, antihyperlipidemic agents, inhibitors of acetyl CoA synthesis, inhibitors of carotenoid biosynthesis, inhibitors of isoprenoid biosynthesis (including inhibitors of sterol biosynthesis), free radical generators, and mixtures thereof.

In one embodiment of the present invention, a mutated negative microorganism capable of overproducing beta-carotene is selected from among all mutated microorganisms by its ability to grow in a medium containing an antihypercholesterolemic agent, an antihyperlipoproteinemic agent, an antihyperlipidemic agent, or a mixture thereof. Antihypercholesterolemic agents, such as lovastatin, typically reduce sterol (e.g., ergosterol) levels in a microorganism. Antihyperlipoproteinemic agents, such as pravastatin and probucol, typically reduce lipoprotein levels in a microorganism. Likewise, antihyperlipidemic agents, such as simvastatin, typically reduce lipid levels in a microorganism. Without being bound by theory, it is believed that microorganisms capable of growing in the presence of these inhibitors are able to shuttle more carbon through the common branch of the carotenoid and sterol biosynthetic pathways. For example, it is believed that microorganisms which are resistant to lovastatin have a modified hydroxy-methyl-glutaryl-coenzyme A (HMG-CoA) reductase enzyme that is no longer inhibited by sterols.

In one embodiment of the present invention, mutated spores are plated onto lovastatin-containing solidified growth medium, such as lovastatin-containing CM17-1, and grown for about 7 days at about 27° C. Preferred concentrations of lovastatin in the medium are from about 30 $\mu$g to about 600 $\mu$g lovastatin per ml medium, and more preferably from about 250 $\mu$g to about 350 $\mu$g lovastatin per ml of medium. Microorganisms able to survive exposure to lovastatin are selected and analyzed for beta-carotene production. Preferably, the selected microorganisms are deep yellow to yellow-orange in color.

Another class of selective agents of the present invention are inhibitors of acetyl CoA synthesis, such as acetate analogs, propionate analogs, and butyrate analogs. Suitable acetyl CoA synthesis inhibitors include, but are not limited to, acetoacetanilide, 2-chloroacetamide, chloroacetate, fluoroacetic acid, and mixtures thereof. A preferred acetate analog is acetoacetanilide. In one embodiment of the present invention, mutated spores are plated onto an acetoacetanilide-containing solidified growth medium, such as acetoacetanilide-containing CM17-1, and grown for about 7 days at about 27° C. Preferred concentrations of acetoacetanilide in the medium are from about 400 $\mu$g to about 800 $\mu$g of acetoacetanilide per ml of medium, and more preferably from about 550 $\mu$g to about 650 $\mu$g of acetoacetanilide per ml of medium. Microorganisms that are able to survive exposure to acetoacetanilide are selected and analyzed for beta-carotene production. Preferably, the selected microorganisms are deep yellow to yellow-orange in color.

In another embodiment, a mutated negative microorganism capable of overproducing beta-carotene is selected from among all mutated microorganisms by its ability to grow in a medium containing inhibitors of the isoprenoid biosynthetic pathway. Isoprenoid pathway inhibitors are compounds that inhibit one or more steps in the isoprenoid synthetic pathway, including steps in the sterol synthetic pathway. Such inhibitors include, but are not limited to: polyene antibiotics, such as nystatin and amphotericin B; antimycin; citrinin; mevinolin; saponin; phosphorylated farnesyl compounds; azasqualenes; allylamine derivatives; thiocarbamates; pyrimidines; imidazoles; triazoles; morpholines; and mixtures thereof. Preferred isoprenoid inhibitors for use in the present invention are nystatin and amphotericin B, which apparently disrupt cellular membranes by binding to membrane-bound ergosterol and other lipids.

In one embodiment, mutated spores are plated on a nystatin-containing solidified growth medium, such as nystatin-containing CM17-1, and grown for about 7 days at about 27° C. Preferred concentrations of nystatin in the medium are from about 0.1 $\mu$g to about 10 $\mu$g nystatin per ml of medium, more preferably from about 0.5 $\mu$g to about 1.0 $\mu$g nystatin per ml of medium, and even more preferably from about 0.7 $\mu$g to about 0.8 $\mu$g nystatin per ml of medium. Microorganisms able to survive exposure to nystatin are selected and analyzed for beta-carotene production. Preferably, the selected microorganisms are deep yellow to yellow-orange in color.

In another embodiment, mutated spores are plated on an amphotericin B-containing solidified growth medium, such as amphotericin B-containing CM17-1, and grown for about 7 days at about 27° C. Preferred concentrations of amphotericin B in the medium are from about 0.1 $\mu$g to about 10 $\mu$g amphotericin B per ml of medium, and more preferably from about 0.5 $\mu$g to about 1.0 $\mu$g amphotericin B per ml of medium. Microorganisms that are able to survive exposure to amphotericin B are selected and analyzed for beta-carotene production. Preferably, the selected microorganisms are deep yellow to yellow-orange in color.

In yet another embodiment of the present invention, a mutated negative microorganism capable of overproducing beta-carotene is selected from among all mutated microorganisms by its ability to grow in a medium containing a compound that inhibits the carotenoid biosynthetic pathway. Inhibitors of the carotenoid biosynthetic pathway are compounds that inhibit one or more steps in the pathway by which carotenoids are synthesized. Carotenoid biosynthesis inhibitors include, but are not limited to: diphenylamine; nicotinic acid; beta-ionone; herbicides, such as norflurazon, metflurazon, phenylfuranones, phenoxynicotinamides, oxyfluorfen, and fluorfen; and mixtures thereof. A preferred carotenoid biosynthesis inhibitor for use in the present invention is beta-ionone. In one embodiment, mutated spores are plated onto beta-ionone-containing solidified growth medium, such as beta-ionone-containing CM17-1, and grown for about 7 days at about 27° C. Preferred concentrations of beta-ionone in the medium are at least about 0.05% beta-ionone. Microorganisms that are able to survive exposure to beta-ionone are selected and analyzed for beta-carotene production. Preferably, the selected microorganisms are deep yellow to yellow-orange in color.

A negative mutated microorganism capable of overproducing beta-carotene can also be selected from among all mutated microorganisms by its ability to grow in a medium containing a compound that generates free radicals (i.e., a free radical generator). It is believed that carotenoids, due to their antioxidant properties, are able to protect cells from damage caused by free radicals. However, the present inventors are unaware of the use of free radical generating compounds to select for microorganisms capable of overproducing beta-carotene. Free radical generators include, but are not limited to, quinones, peroxides, UV light, UV-activated photosynthesizers, X-rays, gamma rays, ozone, and mixtures thereof. Preferred free radical generators, such as quinones and peroxides, are those that are easily absorbed by the microorganisms and apparently are not mutagenic. Of such free radical generators, a preferred free radical generator for use in the present invention is duroquinone. In one embodiment, mutated spores are grown on a solidified growth medium, such as CM17-1, containing from about 1 micromolar ($\mu$M) to about 1 millimolar (mM) duroquinone for about 7 days at about 27° C. Microorganisms able to survive exposure to duroquinone are selected and analyzed for beta-carotene production. Preferably, the selected microorganisms are deep yellow to yellow-orange in color.

In accordance with the present invention, the steps of mutation and selection as described above may be carried out one or more times to produce negative microorganisms having desired characteristics. A preferred embodiment of the present invention is the use of a pooled mutation and selection technique to produce desired microorganisms. According to this technique, the spores of two or more, preferably from about three to about five, negative microorganisms which have already undergone at least one round of mutagenesis and selection are pooled. The pooled spores are exposed to a mutagen, such as NTG, UV light, or EMS, and subsequently exposed to a selective agent from the group described above by plating the spores in a manner such that single colonies form on a solidified growth medium containing the selective agent. Microorganisms able to survive exposure to the selective agent are selected and analyzed for beta-carotene production. Preferably, the selected microorganisms are deep yellow to yellow-orange in color.

In accordance with the mutation/selection strategies of the present invention, negative Mucorales fungal microorganisms, preferably of the genus Blakeslea, and more preferably of the species *Blakeslea trispora*, are produced which are capable of producing at least about 0.15 grams of beta-carotene per liter medium in about 7 days when cultured in an effective production fermentation medium. Preferably, a negative fungal microorganism capable of producing at least about 0.5 grams, more preferably at least about 1.5 grams, and even more preferably at least about 3.0 grams, of beta-carotene per liter of medium in about 7 days, when cultured in an effective production fermentation medium, is isolated. Preferred negative microorganisms are capable of producing at least about 12.5 mg, more preferably at least about 37.5 mg, and even more preferably at least about 75 mg, of beta-carotene per gram dry cell weight when cultured in an effective production fermentation medium. The amounts of beta-carotene that negative microorganisms of the present invention are capable of producing can be determined using the procedures outlined in Example 2.

Preferred negative microorganisms of the present invention comprise negative microorganisms of the genus Blakeslea and mutants thereof, wherein a negative microorganism or a mutant thereof is capable of producing at least about 0.15 grams of beta-carotene per liter in about 7 days when cultured in an effective production fermentation medium.

One preferred negative fungal microorganism of the present invention is *Blakeslea trispora* ATCC No. 74147 (PF17-13) which has an identifying characteristic of being able to produce at least about 2.7 grams of beta-carotene per liter in about 7 days when cultured in an effective production fermentation medium. *B. trispora* ATCC No. 74147 (PF17-13) can also be identified by its capability to produce at least about 65 mg beta-carotene per gram dry cell weight when cultured in an effective production fermentation medium.

Another preferred negative fungal microorganism of the present invention is *Blakeslea trispora* ATCC No. 74146 (PF17-12) which has an identifying characteristic of being able to produce at least about 3 grams of beta-carotene per liter in about 7 days when cultured in an effective production fermentation medium. *B. trispora* ATCC No. 17146 (PF17-12) can also be identified by its capability to produce at least about 75 mg beta-carotene per gram dry cell weight when cultured in an effective production fermentation medium.

*Blakeslea trispora* PF17-12 and *Blakeslea trispora* PF17-13 were deposited with the American Type Culture Collection, ATCC), 12301 Parklawn Drive, Rockville, Md., 20852-1776, on Mar. 25, 1992, and have been designated ATCC No. 17146 (PF17-12) and ATCC No. 17147 (PF17-13) *B. trispora* ATCC No. 74146 and *B. trispora* ATCC No. 74147. Both microorganisms were deposited under the conditions of the Budapest Treaty on the International Recognition of Deposit of Microorganisms for the purpose of Patent Procedure. All restrictions on the availability to the public of the material so deposited will be irrevocably removed upon the granting of a patent. Deposits will be maintained for a time period of 30 years from the date of deposit or 5 years after the last request for the material, whichever is longer.

It is within the scope of the present invention that any mutation/selection and beta-carotene production techniques described herein for *Blakeslea trispora* can be extended to other species of the genus Blakeslea as well as to other microorganisms of the order Mucorales, and particularly to those of the family Choanephoraceae, due to the similarities between microorganisms within the Mucorales order, particularly with respect to the methods by which Mucorales fungal microorganisms produce beta-carotene.

Another aspect of the present invention relates to the culturing of a negative Mucorales fungal microorganism of the present invention to produce beta-carotene and to the recovery of beta-carotene produced thereby.

In order to produce beta-carotene, negative microorganisms of the present invention are first be cultured in the presence of a vegetative fermentation medium effective to promote mycelial growth. When the negative microorganisms have grown to a desired cell density, they are then cultured in a production fermentation medium effective to promote beta-carotene production.

It is within the scope of the present invention that the vegetative and production fermentation media share at least some components. Effective vegetative and production fermentation media are generally aqueous solutions which include assimilable sources of carbon, nitrogen, phosphorus, sulfur, magnesium, and other micronutrients.

Sources of assimilable carbon include, but are not limited to: sugars and their polymers, including starches, dextrin, saccharose, maltose, lactose, glucose, mannose, sorbose, arabinose, xylose, levulose, cellobiose, and molasses; fatty acids; and polyalcohols, such as glycerine. Preferred carbon sources include monosaccharides, disaccharides, and trisaccharides. A more preferred carbon source is glucose.

Sources of assimilable nitrogen include, but are not limited to: inorganic nitrogen compounds, such as ammonium salts; and substances of animal, vegetable and/or microbial origin, such as animal fats, plant oils, protein hydrolysates, microbial biomass hydrolysates, soy meal, fish meal, meat meal, meat extract, peptone, tryptone, corn steep liquor, yeast extract, and amino acids.

Vegetative and production fermentation media can also contain other compounds such as vitamins, growth promoters, antioxidants, surfactants, and/or pigment formation promoters, as appropriate.

In one embodiment of the present invention, negative microorganisms are first cultured in a vegetative fermentation medium effective to promote growth of the respective microorganisms as mycelia and to prepare the microorganisms for maximum productivity in a production fermentation medium. A preferred vegetative fermentation medium for this purpose is VM17-3, which is an aqueous medium comprising corn flour, potassium phosphate, corn steep liquor, junlon (polyacrylic acid), and thiamine. The fermentation is typically conducted at a temperature from about 26° C. to about 28° C., preferably at about 27° C., and at a pH from about pH 3.7 to about pH 3.9, preferably at about pH 3.8. The vegetative fermentation is conducted until the culture grows to a desired density, preferably in the range of from about 8 to about 10 grams dry cell weight per liter. Such a cell density can be typically achieved in about 48 hours.

A portion of the negative microorganism-containing culture is then introduced into a production fermentation medium. As used herein, a production fermentation medium is a medium that is effective in promoting the production of beta-carotene. The production fermentation is preferably conducted at a pH of from about pH 6.2 to about pH 6.7, more preferably at about pH 6.5, and at a temperature of from about 26° C. to about 28° C., more preferably at about 27° C.

When negative microorganisms of the present invention are cultured in the absence of positive microorganisms, it is believed that the negative microorganisms require beta-factor in order to overproduce beta-carotene. Thus, an effective production fermentation medium should include beta-factor. Beta-factor is comprised of trisporic acids, which appear to be breakdown products of beta-carotene. Beta-factor or trisporic acids may be obtained in a variety of ways including, but not limited to, chemical and microbial synthesis. Beta-factor is typically produced upon mating of negative and positive fungal microorganisms and has been shown to stimulate carotenoid biosynthesis in Blakeslea. When culturing negative microorganisms alone, beta-factor is typically added to the production fermentation medium about 54 hours after production culturing was initiated.

In one embodiment of the present invention, beta-factor can be purified from the fermentation medium of a mated culture. For example, cells are removed from a mated culture fermentation medium, preferably by centrifugation. The supernatant is acidified, preferably to about pH 2.0, and mixed with an equal volume of chloroform. The chloroform and aqueous phases are then allowed to separate. The chloroform layer, which contains beta-factor, is condensed and subsequently dissolved in an aqueous buffer to yield a beta-factor containing solution. As used herein, an "effective amount of beta-factor" is that amount of beta-factor required to promote beta-carotene production by negative microorganisms. Typically, the amount of beta-factor added to a fermentation reaction volume is an amount less than or equivalent to the amount of beta-factor harvested from a mated culture fermentation of the same volume.

One production fermentation medium of the present invention, denoted FM17-A, is an aqueous medium comprising Pharmamedia (a cottonseed-derived protein material purchased from Traders Oil Mill Co., Fort Worth, Tex.), glucose, potassium phosphate, manganese sulfate, soybean oil, cottonseed oil, dextrin, Triton X-100, ascorbic acid, lactic acid, thiamine, and isoniazid. A preferred medium is FM17-B in which isoniazid is replaced by kerosene, which appears to stimulate beta-carotene production at least as well as isoniazid. About 48 to about 54 hours after adding the negative microorganisms to the production fermentation medium, beta-factor as well as an antioxidant (preferably ethoxyquin) and a beta-carotene inducer (preferably beta-ionone) are added to the medium. Other suitable beta-carotene inducers include, but are not limited to: citrus derivatives, including citrus pulps and citrus oils, such as limonene; and TCA cycle precursors and intermediates, such as alpha-ketoglutarate.

Another production fermentation medium of the present invention, denoted NM-1, is an aqueous medium comprising cottonseed oil, soybean flour, potassium phosphate, manganese sulfate, and thiamine. About 48 hours to about 54 hours after the initiation of culturing in NM-1, beta-factor and a beta-carotene inducer, such as beta-ionone, is added to the medium. Other beta-carotene inducers can be used as a substitute for, or in addition to, beta-ionone, including, but not limited to: kerosene; isoniazid; citrus derivatives, including citrus pulps and citrus oils, such as limonene; and TCA cycle precursors and intermediates, such as alpha-ketoglutarate.

NM-1 has several advantages including low viscosity, ease of sterilization, and simple composition. Fungi grown in this medium do not clump, despite the low viscosity of the medium.

Beta-carotene production can be accomplished by culturing microorganisms of the present invention in a variety of conventional fermentation modes including, but not limited to, shake flasks, batch fermentors, fed-batch fermentors, and semi-continuous fermentors. It is well known to one skilled in the art that production typically increases when fermentations are carried out in a fermentor as opposed to a shake flask, generally because higher cell densities can be achieved in a fermentor and because the conditions in a fermentor are typically more favorable for faster growth, leading to shorter production times. As such, negative microorganisms of the present invention which are capable of producing at least about 0.15 grams, preferably at least about 0.5 grams, more preferably at least about 1.5 grams, and even more preferably at least about 3 grams, of beta-carotene per liter in about 7 days in a shake flask, are likely capable of producing similar titers in about 4 days in a fermentor.

Beta-carotene production can be measured in several ways, including, but not limited to, spectrophotometric and chromatographic analysis. Spectrophotometry is particularly useful to obtain beta-carotene production levels, such as titers. Reverse phase high performance liquid chromatography is particularly useful both to quantitate beta-carotene production and to distinguish between different beta-carotene species.

Beta-carotene produced in accordance with the present invention can be recovered and used in a variety of ways, including, as an enhancer of pigmentation, as a nutritional (vitamin A) supplement, as an enhancer of lactation, as an enhancer of fertility, as an anticancer agent, as a cardiovascular therapeutic agent, and as an agent to reduce damage caused by reactive oxygen species and phototoxic molecules.

Since beta-carotene is retained within the microorganism after synthesis, beta-carotene can be recovered as a beta-carotene-containing biomass. As used herein, a beta-carotene-containing biomass refers to a composition produced by separating beta-carotene-overproducing microorganisms from a fermentation medium and treating such microorganisms as necessary to make the beta-carotene bioavailable. Suitable separation techniques include, but are not limited to, centrifugation and filtration. As used herein, separation refers to the removal of a substantial amount of medium from the microorganisms.

Suitable treatments include those that result in cell lysis, such as physical, chemical, or enzymatic methods. Treating "as necessary" can range from no treatment to a treatment resulting in complete cell lysis. One of the advantages of Blakeslea is that microorganisms of this genus apparently do not require treatment to make beta-carotene bioavailable, at least for some species to which beta-carotene may be administered. That is, humans and other animals that consume beta-carotene-containing Blakeslea microorganisms are likely to be able to digest Blakeslea cell walls in order to obtain beta-carotene.

In one embodiment, beta-carotene-containing fungal microorganisms are separated from the fermentation medium by rotovap filtration to remove a substantial portion of the liquid, washed with an aqueous solvent, and spray dried to form a substantially dry beta-carotene-containing biomass powder. Preferably the powder contains at least about 3.7% (wt/wt), and more preferably at least about 7.5% (wt/wt), beta-carotene.

Alternatively, beta-carotene can be recovered free from the microorganisms that produced it as a beta-carotene-containing formulation. In one embodiment, beta-carotene-containing Blakeslea are separated from the fermentation medium and lysed. Suitable separation techniques include, but are not limited to, centrifugation and filtration. Lysis can be accomplished using, for example, physical, chemical, or enzymatic methods. Beta-carotene can be extracted from the lysed fungi using an extracting agent and condensed using molecular distillation. Suitable extracting agents include, but are not limited to, supercritical fluids and oil-based solvents, such as sunflower oil, vegetable oils, castor oil and light mineral oil. The recovered beta-carotene-containing formulation is preferably at least about 5% beta-carotene in oil, and more preferably from about 20% to about 30% beta-carotene in oil.

Beta-carotene produced in accordance with the present invention can be used as a feed additive to enhance the pigmentation of animal foodstuffs. As used herein, animal foodstuffs are animals which are raised as food, such as, but not limited to, poultry, fish and crustaceans. Beta-carotene can also be used to enhance the pigmentation of substances such as foods and cosmetics. As used herein, enhancement of pigmentation describes a method by which administration of an effective amount of beta-carotene to a foodstuff or addition of an effective amount of beta-carotene to a substance imparts a yellow to yellow-orange color to the substance (e.g., food products and cosmetics) or to the flesh, skin, other body parts, and/or egg yolks of the animal foodstuff.

Beta-carotene produced according to the present invention can be used as a Vitamin A supplement in animals, such as humans, which are capable of converting beta-carotene into Vitamin A. As used herein, an effective amount of beta-carotene to serve as a Vitamin A supplement, is an amount of beta-carotene which when ingested by an animal and converted into Vitamin A provides sufficient Vitamin A to be an effective Vitamin A supplement.

Beta-carotene can also be administered to animals, such as bovine animals, to increase lactation and fertility in an amount effective to increase lactation or fertility.

In another embodiment of the present invention, beta-carotene produced according to the present invention can be used to prevent or treat cancer or cardiovascular disease or to prevent or reduce damage caused by reactive oxygen species and/or phototoxic molecules. As used herein, reactive oxygen species are molecules that oxidize other molecules, often leading to, or resulting in, cell or tissue damage. Reactive oxygen species include photosensitizers, singlet oxygen, and oxygen free radicals. As used herein, phototoxic molecules refer to agents, such as light, which can degrade or otherwise inactivate light-sensitive compounds, and which can cause tissue damage (including cell and organ damage) in plants and animals. An effective amount of beta-carotene is an amount which effectively prevents or reduces damage caused by reactive oxygen species and phototoxic molecules.

For example, beta-carotene may be used in mammals, preferably humans, to prevent or treat certain forms of cancer or to reduce both external and internal cellular, tissue or organ damage caused by reactive oxygen species, particularly to the cardiovascular system. For example, beta-carotene may be used to lower the incidence of heart attacks. While not being bound by theory, it is believed that the anti-oxidizing activity of beta-carotene can block low density lipoproteins from being deposited as plaque in arteries. Furthermore, beta-carotene may be used to block free radical damage that often occurs after heart attacks.

Beta-carotene-containing biomasses and formulations can be administered either internally (including, but not limited to, oral administration) or externally (including, but not limited to, topical administration). For example, a beta-carotene-containing formulation can be added to sunscreens and other oils and lotions to reduce damage to the skin caused by reactive oxygen species.

Beta-carotene-containing formulations can also be contacted with (e.g, added to) light-sensitive and/or oxygen-sensitive compounds, including foods, in an effective amount to stabilize and reduce damage caused to such compounds in the presence of light or oxygen.

The following experimental results are provided for purposes of illustration and are not intended to limit the scope of the invention.

EXAMPLE 1

This Example describes the use of mutation and selection strategies of the present invention to produce several negative *Blakeslea trispora* microorganisms, including *B. trispora* ATCC No. 74146 and *B. trispora* ATCC No. 74147 (PF17-13).

Negative microorganism *Blakeslea trispora* ATCC No. 14272 was subjected to multiple rounds of mutation and selection, leading to the production of negative microorganisms 13-29, 13-36, 13-75, 13-109, and 13-113, as shown in Table 1. Spore suspensions of these five negative microorganisms were pooled and submitted to mutagenesis using NTG (N-methyl-N'-nitro-N-nitrosoguanidine), as shown in Table 2a.

TABLE 1

Genealogy of Negative Microorganisms

```
                    ATCC 14272
                       | NTG
                      14-38
                       | NTG
                     28-163
              ┌────────┴────────┐
              | EU              | Re
             4-76              16-9
              | NTG             | NTG
            15-73              29-104
              | Re
             21-9
              |
       ┌──────┴──────┐
       | Re          | NTG
      36-13         36-42
       | Re          | Re
      50-10         50-15
       | UV          | NTG
      84-62         66-133
       | NTG         | Re
     101-222        86-67
       | Re          | Re
       8-28         96-19
       | NTG         | LovR(spon.)
      19-98         6-142
       | NTG
      35-88

┌──────────────────────┬──────────────┐
       | UV                                  | Re
                                            79-273
                                             | Re
      50-28          52-108                 85-2
       | UV           | NTG                  | Re
      72-248         76-12                  9-1
      (NysR)          | Re
       | NTG         80-5
   ┌───┴───┐          | NTG
   78-144  78-122    5-203
   | Re     | Re       |
  88-199   89-2    ┌───┼────────┬──────────┐
                   | Re  | NTG  | NTG
                  13-75 13-109  (DQR)
   | Re    | NTG  13-113        13-29
  10-4    (LovR)                13-36
          11-134
```

NysR: nystatin resistant mutant
LovR: lovastatin resistant mutant
DQR: duroquinone resistant mutant
EU: UV and ethylmethane sulfonate
NTG: N-methyl-N'-nitro-nitrosoguanidine
Re: reisolate of parental strain

TABLE 2

Pooling of Negative Microorganisms a. Pool of 13-29, 13-36, 13-75, 13-109, and 13-113
```
            | NTG
      ┌─────┴─────┐
    25-28       25-38
    (LovR)      (AcetoR)
``` b. Pool of 13-29, 13-36, 13-75, 13-109, and 13-113
```
            | NTG
      ┌─────┴─────┐
    25-20       25-123
    (LovR)
``` c. Pool of 25-20, 25-28, 25-38, and 25-123
```
            |
      ┌─────┴─────┐
     | Re         | NTG
   <PF17-12>    35-6 (LovR)
``` d. Pool of 9-1, 10-4, 11-134, 13-109, and 19-42
```
                    | NTG
      ┌─────────────┼─────────────┐
   31-9 (β-ioR)  <PF17-13> (LovR)  32-38 (AcetoR)
   31-32 (β-ioR)
``` e. Pool of 35-88, 89-2, and 5-203
```
            | NTG
          19-42
         (LovR)
```

LovR: lovastatin resistant mutant
AcetoR: acetoacetanilide resistant mutant
β-ioR: β-ionone resistant mutant
Re: reisolate of parental strain Spore suspensions were obtained by thawing vials of frozen spores preserved in a solution of 10% glycerol and 5% lactose. For each microorganism, about 0.1 ml of spores were pipetted onto a PDA slant. APDA slant contains, per liter of water, 39 grams of Difco ™ potato dextrose agar, 2 mg of thiamine·HCl, and 5 g of Bacto ™ -agar, at a final pH of about pH 5.9. The spore-containing PDA slants were incubated at about 27° C. for at least about 6 days. Five ml of sterile water was then added to the slant to suspend the spores. The concentration of spores in the suspension was about $3 \times 10^5$ spores per ml.

A suspension containing about 50,000 spores of negative *B. trispora* microorganisms 13-29, 13-36, 13-75, 13-109, and 13-113 was centrifuged and the spores resuspended in 5 ml of 50 mM Tris (hydroxymethyl)aminomethane (Tris) buffer at a pH of about 8.0. NTG was added to a final concentration of about 50 µg NTG per ml of buffer, and the spores were incubated for about 20 to 25 minutes at room temperature. (These conditions typically kill 30% to 60% of the cells.) The mutated spores were washed in 100 mM phosphate buffer at about pH 7.0, prior to spreading onto CM17-1 solidified growth media plates that also contained either about 300 µg lovastatin per ml of medium or about 600 µg acetoacetanilide per ml of medium in order to identify negative microorganisms capable of overproducing beta-carotene. CM17-1 contains, per liter of water, 3 grams of glucose, 200 mg of L-asparagine, 50 mg of MgSO₄·7H₂O, 150 mg of KH₂PO₄, 25 µg thiamine·HCl, 100 mg of yeast extract, 100 mg of sodium deoxycholate, and 20 grams of agar. The pH of CM17-1 is about pH 5.3 to about pH 5.5. The lovastatin-containing or acetoacetanilide-containing CM17-1 plates were incubated at about 27° C. for about 6 to about 8 days and colonies having a color indicative of beta-carotene production were isolated.

A yellow-orange negative microorganism, denoted B. trispora 25-38, was isolated from the acetoacetanilide-containing plate. A deep yellow negative microorganism, denoted B. trispora 25-28, was isolated from the lovastatin-containing plate. B. trispora 25-28 produced at least about 2.7 grams of beta-carotene per liter in about 7 days when cultured in a shake flask in an effective production fermentation medium as described in Example 2.

In a second pooling experiment using spore suspensions of B. trispora negative microorganisms 13-29 13-36 13-75, 13-109, and 13-113 (see Table 2b), the pooled spores were exposed to NTG as described above, plated on CM17-1 solidified growth medium either with or without about 300 μg lovastatin per ml of medium, and incubated for about 6 to about 8 days at about 27° C. One negative microorganism, denoted B. trispora 25-20, was isolated from a plate containing lovastatin. A second negative microorganism, denoted B. trispora 25-123, was isolated from a plate without lovastatin.

Spore suspensions of B. trispora negative microorganisms 25-28 and 25-38 were mixed with spore suspensions of B. trispora negative microorganisms 25-20 and 25-123, as shown in Table 2c. The pooled mixture was exposed to NTG as described above, spread onto CM17-1 plates, and incubated for about 6 to about 8 days at about 27° C. to isolate colonies with pigmentation indicative of beta-carotene production. A dark yellow negative microorganism, denoted B. trispora ATCC No. 74146 (PF17-12) was isolated. B. trispora ATCC No. 74146 (PF17-12) produced at least about 3 grams of beta-carotene per liter in about 7 days, and at least about 75 mg beta-carotene per gram dry cell weight, when cultured in a shake flask in an effective production fermentation medium as described in Example 2.

In another pooled mutation/selection experiment, a pooled spore suspension of B. trispora negative microorganisms 9-1, 10-4, 11-134, 13-109, and 19-42 were exposed to NTG as described above (see Table 2d; also see Tables 1 and 2e for the genealogies of 9-1, 10-4, 11-134, 13-109, and 19-42). Mutated spores were spread onto CM17-1 plates containing either 0.1% beta-ionone, 300 μg lovastatin per ml, or 600 μg acetoacetanilide per ml, and incubated at about 27° C. for about 6 to about 8 days to identify negative microorganisms capable of overproducing beta-carotene. Two yellow negative microorganisms, denoted B. trispora 31-9 and 31-22, were isolated from beta-ionone-containing CM17-1 medium. A dark yellow negative microorganism, denoted B. trispora 32-38, was isolated from acetoacetanilide-containing CM17-1 medium. A yellow-orange negative microorganism, denoted B. trispora ATCC No. 74147 (PF17-13), was isolated from lovastatin-containing CM17-1 medium.

B. trispora ATCC No. 74147 (PF17-13) produced at least about 2.7 grams of beta-carotene per liter in about 7 days, and at least about 65 mg beta-carotene per gram dry cell weight, when cultured in a shake flask in an effective production fermentation medium as described in Example 2.

EXAMPLE 2

This Example describes the production of beta-carotene using B. trispora ATCC No. 74146 (PF17-12).

A two-stage fermentation was carried out to produce beta-carotene using negative B. trispora ATCC No. 74146 (PF17-12). In the first (vegetative growth) phase, a 250–300 ml non-baffled shake flask containing about 30 ml of VM17-3 vegetative fermentation medium was inoculated with about 0.5 ml of a B. trispora ATCC No. 74146 (PF17-12) spore suspension (about $2 \times 10^4$ spores). VM17-3 medium contains, per liter water, 35 grams of corn flour, 500 mg of $KH_2PO_4$, 2.5 grams of corn steep powder, 2 grams of junlon (polyacrylic acid), and 2 mg of thiamine·HCl, at a pH of about pH 3.7 to about pH 3.9. B. trispora ATCC No. 74146 (PF17-12) microorganisms were cultured in a New Brunswick Scientific G-53 shaker at about 250 rpm for about 48 hours at about 27° C. in a high humidity environment (about 60% to about 80% humidity), and achieved a cell density of from about 8 to about 10 grams dry cell weight per liter of medium.

In the second (production) stage, 2 ml of the vegetatively grown B. trispora ATCC No. 74146 (PF17-12) culture was removed from the VM17-3 medium and added to 30 ml of FM17-A production fermentation medium in a 250–300 ml non-baffled shake flask. FM17-A medium contains, per liter water, 75 grams of Pharmamedia, 10 grams of glucose, 100 mg of $MnSO_4 \cdot H_2O$, 500 mg of $KH_2PO_4$, 30 grams (w/v) of soybean oil, 30 grams (w/v) of cottonseed oil, 60 grams of dextrin, 1.2 grams (w/v) of Triton X-100, 6 grams (w/v) of ascorbic acid, 2 grams (w/v) of lactic acid, 2 mg of thiamine·HCl, and 0.075% isoniazid. The medium is adjusted to a pH of about pH 6.5 with 50% sodium hydroxide.

The culture was incubated at about 27° C. at about 250 rpm in a New Brunswick Scientific G-53 shaker. About 54 hours after culturing was initiated in FM17-A medium, beta-ionone (0.1%), ethoxyquin (0.025%), and about 2 ml of beta-factor were added to the medium. The fermentation was continued for an additional 5 days.

Beta-factor was prepared by extraction from 1500 ml of a production fermentation medium (e.g., FM17-A or FM17-B) in which negative and positive B. trispora microorganisms had been mated. Approximately 144 hours after mating, the fermentation medium was centrifuged at 10,000 rpm for 15 minutes to separate the microorganisms from the medium, thereby obtaining a beta-factor-containing supernatant. The beta-factor-containing supernatant (about 1000 ml) was adjusted to pH 2.0. About 1000 ml of chloroform was added to the pH-adjusted supernatant. The two phases were mixed in order to permit the chloroform to extract the beta-factor from the aqueous supernatant and subsequently separated by centrifugation (10,000 rpm for 5 minutes). The beta-factor-containing chloroform phase was condensed, and the beta-factor dissolved in 100 ml of sterile 0.1M Tris buffer, pH 7.5.

Beta-carotene production was measured using the following procedure. About 8 ml of the mated culture is homogenized for about 20 seconds at 75% maximum speed with a Brinkmann" homogenizer in a 15 ml polycarbonate tube. About 0.1 ml of the homogenate is transferred into a previously tared $16 \times 125$ mm screw cap test tube containing about 10 4-mm glass beads. The weight of the homogenate is recorded to at least three significant figures and typically is about 0.100 grams ±0.05 grams. The homogenate is vortexed for about 5 minutes on a multi-tube vortexer set at about 90% maximum speed. About four ml of ethanol are added and vortexing is continued for an additional 20 seconds. About four ml of hexane containing 1 mg/ml butylated hydroxytoluene (hexane/BHT) is then added and the sample vortexed for an additional 5 minutes. About one ml of water is then added, followed by mild hand mixing. The tube is then centrifuged at 2,000 rpm for about 2 minutes in order to separate the beta-carotene-containing hexane phase. A sample of the hexane phase is diluted with hexane, typically at a dilution factor of about 100-fold. The absorbance of the sample at about 450 nm is then determined, and the beta-carotene concentration calculated. The extinction coefficient for beta-carotene is determined experimentally by dissolving a known weight of pure carotenoid in hexane, and measuring the absorbance at about 450 nm. Under these conditions, the extinction coefficient is about 2620. Typically, beta-carotene production values are confirmed by reverse phase high performance liquid chromatography (HPLC) analysis.

*B. trispora* ATCC No. 74146 (PF17-12), cultured under these conditions, typically produces about 2 grams of beta-carotene per liter, and is capable of producing at least about 3 grams of beta-carotene per liter.

While various embodiments of the present invention have been described in detail, it is apparent that modifications and adaptations of those embodiments will occur to those skilled in the art. It is expressly understood, however, that such modifications and adaptations are within the scope of the present invention, as set forth in the following claims:

What is claimed is:

1. A beta-carotene-containing biomass produced by a method comprising:
    (a) culturing in an effective production fermentation medium a negative Blakeslea microorganism selected from the group consisting of *Blakeslea trispora* PF17-12 (ATCC No. 74146), *Blakeslea trispora* PF17-13 (ATCC No. 74147), and mutants thereof which are capable of producing at least about the same levels of beta-carotene as *Blakeslea trispora* PF17-12 (ATCC No. 74146) and *Blakeslea trispora* PF17-13 (ATCC No. 74147) respectively; and
    (b) separating the microorganism from the medium to form a beta-carotene-containing biomass.

2. The beta-carotene-containing biomass of claim 1, wherein the negative Blakeslea microorganism is capable of producing at least about 0.5 grams of beta-carotene per liter in fermentation medium.

3. The beta-carotene-containing biomass of claim 1, wherein the biomass comprises at least about 3.7% (wt/wt) beta-carotene.

4. The beta-carotene-containing biomass of claim 1, wherein the biomass comprises at least about 7.5% (wt/wt) beta-carotene.

5. A negative Blakeslea microorganism having all of the identifying characteristics of *Blakeslea trispora* PF17-13 (ATCC No. 74147).

6. The microorganism of claim 5 which is capable of producing at least about 0.5 grams of beta-carotene per liter in about 7 days when cultured in an effective production fermentation medium.

7. The microorganism of claim 5 which is capable of producing at least about 1.5 grams of beta-carotene per liter of medium in about 7 days when cultured in an effective production fermentation medium.

8. The microorganism of claim 5 which is capable of producing at least about 2.7 grams of beta-carotene per liter of medium in about 7 days when cultured in an effective production fermentation medium.

9. The microorganism of claim 5 which is capable of producing at least about 12.5 grams of beta-carotene per gram dry cell weight when cultured in an effective production fermentation medium for about 7 days.

10. The microorganism of claim 5 which is capable of producing at least about 65 mg of beta-carotene per gram dry cell weight when cultured in an effective production fermentation medium for about 7 days.

11. The microorganism of claim 5 which is *Blakeslea trispora* PF17-13 (ATCC No. 74147).

12. A biologically pure culture of *Blakeslea trispora* PF17-13 (ATCC No. 74147), or a mutant thereof, which is capable of producing at least about 0.5 grams of beta-carotene per liter in about 7 days when cultured in an effective production fermentation medium.

13. The culture of claim 12 which is capable of producing at least about 2.7 grams of beta-carotene per liter of medium in about 7 days when cultured in an effective production fermentation medium.

14. A negative Blakeslea microorganism having all of the identifying characteristics of *Blakeslea trispora* PF17-12 (ATCC No. 74146).

15. The microorganism of claim 14 which is capable of producing at least about 0.5 grams of beta-carotene per liter in about 7 days when cultured in an effective production fermentation medium.

16. The microorganism of claim 14 which is capable of producing at least about 1.5 grams of beta-carotene per liter of medium in about 7 days when cultured in an effective production fermentation medium.

17. The microorganism of claim 14 which is capable of producing at least about 3 grams of beta-carotene per liter of medium in about 7 days when cultured in an effective production fermentation medium.

18. The microorganism of claim 14 which is capable of producing at least about 12.5 mg of beta-carotene per gram dry cell weight when cultured in an effective production fermentation medium for about 7 days.

19. The microorganism of claim 14 which is capable of producing at least about 75 mg of beta-carotene per gram dry cell weight when cultured in an effective production fermentation medium for about 7 days.

20. The microorganism of claim 14 which is *Blakeslea trispora* PF17-12 (ATCC No. 74146).

21. A biologically pure culture of *Blakeslea trispora* PF17-12 (ATCC No. 74146), or a mutant thereof, which is capable of producing at least about 0.5 grams of beta-carotene per liter in about 7 days when cultured in an effective production fermentation medium.

22. The culture of claim 21 which is capable of producing at least about 3 grams of beta-carotene per liter of medium in about 7 days when cultured in an effective production fermentation medium.

* * * * *

UNITED STATES PATENT AND TRADEMARK OFFICE
CERTIFICATE OF CORRECTION

PATENT NO. : 5,328,845
DATED : July 12, 1994
INVENTOR(S) : Mark Finkelstein, et al.

It is certified that error appears in the above-indentified patent and that said Letters Patent is hereby corrected as shown below:

Column 18, line 12, delete "grams" and insert --mg--.

Signed and Sealed this

First Day of November, 1994

*Attest:*

*Attesting Officer*

BRUCE LEHMAN

*Commissioner of Patents and Trademarks*